(12) United States Patent
Mehta et al.

(10) Patent No.: US 8,541,632 B2
(45) Date of Patent: Sep. 24, 2013

(54) PROCESS AND APPARATUS FOR PRODUCING CHLOROHYDRIN

(75) Inventors: Anil J. Mehta, Lake Jackson, TX (US); Danil Tirtowidjojo, Lake Jackson, TX (US); Bruce D. Hook, Lake Jackson, TX (US); John R. Briggs, Midland, MI (US); Jeffrey G. Hippler, South Charleston, WV (US)

(73) Assignee: Dow Global Technologies LLC, Midland, MI (US)

( * ) Notice: Subject to any disclaimer, the term of this patent is extended or adjusted under 35 U.S.C. 154(b) by 514 days.

(21) Appl. No.: 12/595,430

(22) PCT Filed: Apr. 11, 2008

(86) PCT No.: PCT/US2008/059981
§ 371 (c)(1),
(2), (4) Date: Aug. 24, 2010

(87) PCT Pub. No.: WO2009/002585
PCT Pub. Date: Dec. 31, 2008

(65) Prior Publication Data
US 2011/0004027 A1    Jan. 6, 2011

Related U.S. Application Data

(60) Provisional application No. 60/923,103, filed on Apr. 12, 2007.

(51) Int. Cl.
*C07C 311/36*    (2006.01)

(52) U.S. Cl.
USPC .......................................... 568/841; 568/844

(58) Field of Classification Search
USPC .................................................. 568/844, 841
See application file for complete search history.

(56) References Cited

U.S. PATENT DOCUMENTS 4,496,753 A    1/1985    Kwon et al.

FOREIGN PATENT DOCUMENTS

| | | |
|---|---|---|
| DE | 197308 | 11/1906 |
| EP | 1752435 | 2/2007 |
| EP | 1762556 | 3/2007 |
| WO | 2005021476 | 3/2005 |
| WO | 2005054167 | 6/2005 |
| WO | 2006020234 | 2/2006 |

*Primary Examiner* — Shawquia Young

(57) ABSTRACT

A process and apparatus for producing chlorohydrin comprising reacting a multihydroxylated-aliphatic hydrocarbon-containing stream with a stream of a first effluent exiting from a hydrochlorination reactor in at least one vessel wherein the vessel exhibits a plug flow residence time characteristic, under conditions such that at least a portion of any unreacted HCl component present in the first effluent is reacted with the multihydroxylated-aliphatic hydrocarbon present in the multihydroxylated aliphatic hydrogen-containing stream to from an amount of monochlorohydrin in a stream of a second effluent exiting from the plug flow vessel; recovering said second effluent; and then optionally using the second effluent from the plug flow reactor in a subsequent processing operation.

9 Claims, 4 Drawing Sheets

PROCESS AND APPARATUS FOR PRODUCING CHLOROHYDRIN

CROSS REFERENCE TO RELATED APPLICATIONS

This is a §371 application of PCT International Patent Application Number PCT/US2008/059981 filed Apr. 11, 2008, and claims priority from provisional application Ser. No. 60/923,103 filed Apr. 12, 2007, each of which is incorporated herein by reference in its entirety.

FIELD OF INVENTION

The present invention relates to a process for producing a chlorohydrin by reacting a multihydroxylated-aliphatic hydrocarbon such as glycerol with a chlorinating agent-containing stream. More specifically, the present invention relates to a process for producing a chlorohydrin by reacting a multihydroxylated-aliphatic hydrocarbon such as glycerol and a chlorinating agent-containing stream, the reaction being carried out in a vessel having a plug flow residence time characteristic, wherein the chlorinating agent-containing stream is at least a portion of an effluent comprising a reaction mixture originating from a hydrochlorination process. The chlorinating agent in the stream can be for example unreacted hydrogen chloride (HCl) dissolved in the reaction mixture effluent and the effluent mixture may be an effluent exiting a hydrochlorination reactor(s). Additionally, the present invention reaction is preferably carried out before subjecting the effluent for further processing such as distillation for separation of the chlorohydrin from other components present in the stream. In a specific embodiment, the HCl reacts with the multihydroxylated-aliphatic hydrocarbon such as glycerol to produce mainly monochlorohydrin, also referred to as monochloropropanediol. The monochlorohydrin is in turn converted to dichlorohydrin which is eventually used for producing epichlorohydrin.

BACKGROUND OF THE INVENTION

It is well known to produce dichlorohydrins by reacting glycerol with hydrogen chloride (HCl) in the presence of a catalyst. The dichlorohydrins, which are also often referred to as dichloropropanols, are reaction intermediates that can then be used to prepare an epoxide such as epichlorohydrin. Epichlorohydrin, in turn, is a well known compound used for making epoxy resins for various end-use applications.

For example, German Patent No. 197308 teaches a process for preparing a chlorohydrin by the catalytic hydrochlorination of glycerin by means of anhydrous hydrogen chloride. WO 2005/021476 describes a continuous process for preparing the dichloropropanols by hydrochlorination of glycerin and/or monochloropropanediols with gaseous hydrogen chloride with catalysis of a carboxylic acid. WO 2005/054167 also describes a process for producing dichloropropanols from glycerol.

WO 2006/020234 A1 describes a superatmospheric pressure process for conversion of a glycerol or an ester or a mixture thereof to a chlorohydrin, comprising the step of contacting a multihydroxylated-aliphatic hydrocarbon, an ester of a multihydroxylated-aliphatic hydrocarbon, or a mixture thereof with a source of a superatmospheric partial pressure of hydrogen chloride to produce a chlorohydrin, an ester of a chlorohydrin, or a mixture thereof in the presence of an organic acid catalyst without substantially removing water.

FIG. 1 shows an embodiment of the process taught by WO 2006/020234 A1 in which a vessel 36 is fed with a feed stream 31, containing hydrogen chloride; and a recycle stream containing glycerol, glycerol esters, monochlorohydrin and their esters and catalyst, via stream 35. In vessel 36, which may comprise one or more CSTRs (Continuous Stirred Tank Reactors), one or more tubular reactors or combinations thereof, glycerol and monochlorohydrins are converted to dichlorohydins. Stream 32, containing, for example, dichlorohydrins, monochlorohydrins, glycerol and their esters, catalyst, unreacted hydrogen chloride and water exits vessel 36 and is fed to vessel 37. Also fed to vessel 37 is feed stream 33, containing glycerol.

The reaction mixture exiting the dichlorohydrin reactor(s) [reactor vessel 36 in FIG. 1] described in WO 2006/020234 A1, where primarily dichlorohydrin is formed from the reaction of glycerol and monochlorohydrin with HCl, is a mixture of components containing, dichlorohydrins, monochlorohydrins, glycerol and their esters, catalyst, water and unreacted hydrogen chloride as described above. A significant amount of hydrogen chloride (HCl) remains dissolved and unreacted in the reaction mixture because of phase equilibrium between the liquid and the vapor phases in the hydrochlorination reactor(s). The concentration of HCl present in the liquid phase (reaction mixture) can be, for example, in the range of 5-20% by mass, depending on the exact conditions in the reactor such as temperature, pressure and compositions of liquid and vapor phases in the reactor. The HCl present in the reaction effluent, if not used efficiently in the process to the maximum possible extent before forwarding the reaction effluent to a distillation column, will exit the distillation system as a light product. This HCl will exit the top of the distillation column either with the dichlorohydrin product or as uncondensed vapors or both. This HCl is a loss for the process if not recovered and recycled to the process. Additionally, this HCl must be neutralized in a downstream process or in suitable equipment if not recovered and recycled, imposing additional expense to running the process. If this HCl loss is substantial for the process, then the HCl needs to be recovered and recycled to the process to keep the process economical. Recovering and recycling unreacted HCl from the reaction effluent or the distillation column product is very expensive as HCl is wet and, therefore, very corrosive to the equipment required for recovery. Only equipment made of glass lined, Teflon® lined or other suitable plastic lined materials or of exotic metals and alloys such as tantalum, zirconium and Hastelloy™ (trademarked by High Performance Alloys, Inc.) can be used in the process for recovering and recycling HCl, imposing a high cost on the process. Therefore, minimizing HCl in the feed stream to a separation system such as a distillation column without having to recover the HCl is advantageous and overall the least expensive option.

WO 2006/020234 A1, on lines 7-20 of page 26, describes a second vessel where the primary purpose of the second vessel is to convert esters of monochlorohydrins and dichlorohydrins to liberate free monochlorohydrins and dichlorohydrins. See FIG. 1. WO 2006/020234 A1 also states that at least some of the unreacted hydrogen chloride that enters the vessel is also consumed to form mainly monochlorohydrins. WO 2006/020234 A1 further states that the second vessel (vessel 37) may also serve as a means to separate the desired dichlorohydrins from unreacted monochlorohydrins and glycerol and their esters. Vessel 37 may include, for example, one or more distillation columns, flash vessels, extractors, or any other separation equipment; or vessel 37 may be, for example, a combination of a stirred tank, tubular reactor or similar vessel with the aforementioned separation equipment.

WO 2006/020234 A1 neither specifies a process sequence to be followed for the reaction and separation of the desired dichlorohydrins, in the process nor does it distinguish between the type of vessels to be used for the purpose of reacting the effluent of the primarily dichlorohydrin producing reactor(s) with glycerol (or a glycerol-containing stream). WO 2006/020234 A1 does not specify whether the reaction with glycerol is carried out prior to or simultaneously with the separation of dichlorohydrins. The prior known process described in WO 2006/020234 A1 does not specifically use a reactor for the purpose of reacting HCl dissolved in the dichlorohydrin reaction effluent with glycerol for improving HCl utilization in the process and more over, the prior art processes do not use a plug flow reactor for reacting dichlorohydrin reaction effluent with glycerol.

Accordingly, it is desired to provide an improved process with more specific process steps and type of equipment to be used in the process such as using a plug flow reactor for the purpose of reacting HCl dissolved in the dichlorohydrin reaction effluent with glycerol for improving HCl utilization; and it is desired to provide a more efficient, smaller, simpler and a much cheaper reactor for reacting HCl in the dichlorohydrin reaction effluent with glycerol. The present invention is, however, not limited to the production of dichlorohydrins only; it is also useful in the production of monochlorohydrins, for example.

It is also desired to provide a significant reduction in the capital and the operating cost of a glycerol hydrochlorination process which can be integrated into a process for producing epichlorohydrin; and it is desired to provide a more efficient and lower cost process to produce epichlorohydrin from glycerol.

SUMMARY OF THE INVENTION

The previously known prior art processes are improved by providing a process in which the HCl dissolved and unreacted in a hydrochlorination reactor effluent is first reacted with a multihydroxylated-aliphatic hydrocarbon such as glycerol in a multihydroxylated-aliphatic hydrocarbon-containing stream such as a glycerol-containing stream, forming mainly monochlorohydrin, before separating the dichlorohydrins from the reaction effluent in a separation system such as a distillation column. The prior art is further improved by providing a specific type of reactor for the reaction, for example, comprising reacting HCl with glycerol to monochlorohydrin, the $1^{st}$ reaction step in the hydrochlorination of glycerol to dichlorohydrin process. It has been found that using a plug flow reactor (PFR) vessel for this $1^{st}$ reaction step has a significant advantage over using other types of reactors such as a continuous stirred tank reactor (CSTR). A plug flow reactor provides a huge reduction in vessel volume compared to a CSTR for the same reaction efficiency. The reduction in the vessel volume can be, for example, five fold. A plug flow reactor is much simpler and cheaper to construct and operate than a continuous stirred tank reactor providing a significant reduction in capital and operating cost of the process.

One aspect of the present invention is using a plug flow type reactor vessel for carrying out the first reaction step on the reaction effluent before forwarding the reaction effluent to a subsequent processing for example a separation system such as a distillation column. Thus, the present invention provides a more efficient, smaller, simpler and a cheaper reactor for reacting HCl in the dichlorohydrin reaction effluent with a multihydroxylated hydrocarbon such as glycerol which, in turn, provides a more efficient and lower cost process to produce epichlorohydrin from glycerol, or more generally, hydrochlorination of multihydroxylated hydrocarbons.

Another aspect of the present invention is directed to a process for producing chlorohydrins including feeding a glycerol-containing stream and a stream of a first effluent exiting from at least a first chlorohydrin producing hydrochlorination reactor into at least a second hydrochlorination reactor; wherein the second reactor is a plug flow reactor, under conditions such that at least a portion of any unreacted HCl component present in the first effluent is reacted with the glycerol to form an amount of monochlorohydrin in a stream of a second effluent exiting from the plug flow reactor; and passing the second effluent from the plug flow reactor to a subsequent processing step.

Another aspect of the present invention is directed to a process for producing chlorohydrins including the steps of:

(a) reacting a first multihydroxylated-aliphatic hydrocarbon-containing stream with HCl in the presence of a catalyst in one or more hydrochlorination reactor(s) forming a first effluent from said hydrochlorination reactor(s);

(b) feeding the first effluent from the hydrochlorination reactor to a plug flow reactor;

(c) feeding a second multihydroxylated-aliphatic hydrocarbon-containing stream to the plug flow reactor such that at least a portion of any unreacted HCl present in the first effluent stream is reacted with the multihydroxylated-aliphatic hydrocarbon present in the second multihydroxylated-aliphatic hydrocarbon-containing stream in the plug flow reactor forming a second effluent stream from the plug flow reactor; and (d) passing the second effluent from the plug flow reactor to a subsequent processing step.

Yet another aspect of the present invention is directed to a process for producing chlorohydrins including the steps of:

(a) reacting a first multihydroxylated-aliphatic hydrocarbon-containing stream with HCl in the presence of a catalyst in one or more hydrochlorination reactor(s) forming a first effluent from said reactor;

(b) feeding the first effluent from the hydrochlorination reactor to a plug flow reactor;

(c) feeding a second multihydroxylated-aliphatic hydrocarbon-containing stream to the plug flow reactor such that at least a portion of any unreacted HCl present in the first effluent stream is reacted with the multihydroxylated-aliphatic hydrocarbon present in the second multihydroxylated-aliphatic hydrocarbon-containing stream in the plug flow reactor forming a second effluent stream from the plug flow reactor;

(d) feeding the second effluent from the plug flow reactor to a separation vessel wherein a product stream is separated from a third effluent stream containing unreacted or monochlorinated multihydroxylated-aliphatic hydrocarbon; and (e) recovering the product stream from the separation vessel.

Still another aspect of the present invention is directed to a process for producing an epoxide comprising the steps of:

(a) reacting a first multihydroxylated-aliphatic hydrocarbon-containing stream with HCl in the presence of a catalyst in one or more hydrochlorination reactor(s) forming a first effluent from said reactor;

(b) feeding the first effluent from the hydrochlorination reactor to a plug flow reactor;

(c) feeding a second multihydroxylated-aliphatic hydrocarbon-containing stream to the plug flow reactor such that at least a portion of any unreacted HCl present in the first effluent stream is reacted with the multihydroxylated-aliphatic hydrocarbon present in the second multihydroxylated-aliphatic hydrocarbon-containing stream in the plug flow reactor forming a second effluent stream from the plug flow reactor;

(d) feeding the second effluent from the plug flow reactor to a separation vessel wherein a product stream is separated from a third effluent stream containing unreacted or monochlorinated multihydroxylated-aliphatic hydrocarbon;

(e) adding a alkali metal hydroxide source or an alkaline earth metal hydroxide source to the product stream from the separation vessel to form an epoxide; and (f) recovering the epoxide.

Another aspect of the present invention relates to an apparatus suitable for producing chlorohydrin from multihydroxylated-aliphatic hydrocarbon compound(s) and/or esters (s) thereof comprising:

(a) at least one hydrochlorination reactor;

(b) at least one vessel which exhibits a plug flow residence time characteristic; wherein the at least one vessel is connected directly or indirectly to the hydrochlorination reactor for conducting a stream comprising a first effluent exiting from a hydrochlorination reactor to said at least one vessel;

(c) a means for conducting a multihydroxylated-aliphatic hydrocarbon-containing stream into said at least one vessel such that a reaction is carried out in the at least one vessel; wherein the at least one vessel exhibits a plug flow residence time characteristic, and wherein at least a portion of any unreacted HCl component present in the first effluent is depleted by a reaction with the multihydroxylated-aliphatic hydrocarbon present in the multihydroxylated-aliphatic hydrocarbon-containing stream to form an amount of monochlorohydrin in a stream comprising a second effluent exiting from the at least one vessel; and (d) means for recovering the second effluent from the at least one vessel.

The present invention provides a more structured process using a specific type of equipment in the process such as using a plug flow reactor for example, in a process for reacting dissolved HCl present in the reaction mixture exiting the hydrochlorination reactor(s) with a multihydroxylated-aliphatic hydrocarbon such as glycerol to improve HCl efficiency in the process. It has been found that by using a plug flow reactor instead of an alternative such as a CSTR, a huge reduction in vessel volume, a five fold reduction for example, is obtained for the same reaction efficiency. A plug flow reactor is much simpler and cheaper to construct and operate than a continuous stirred tank reactor. This plug flow reactor is critical in maximizing HCl yield in the glycerol hydrochlorination process which in turn is a critical step in the process for production of epichlorohydrin from glycerol. The glycerol hydrochlorination process is extremely corrosive and, therefore, requires very expensive materials of construction. Using a vessel of a much less volume such as a pipe of one fifth of the volume, compared to a large vessel such as a CSTR made of expensive material of construction goes a long way in reducing capital and operating cost of the glycerin to epichlorohydrin process.

BRIEF DESCRIPTION OF THE DRAWINGS

The following drawings are presented to illustrate the prior art and the present invention. However, it should be understood that the present invention is not limited to the precise arrangements shown in the drawings.

DETAILED DESCRIPTION OF THE PREFERRED EMBODIMENTS

Figure 1:
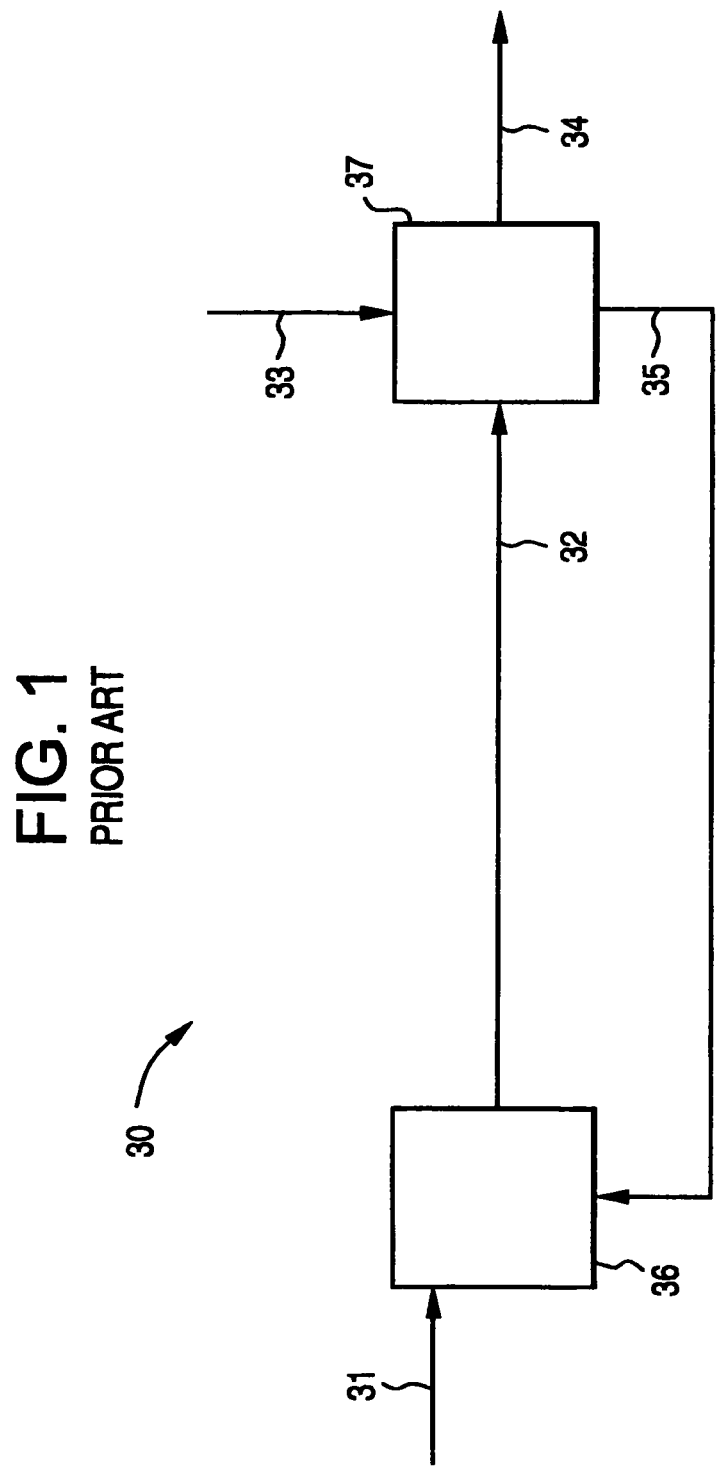
FIG. 1 is a simplified block flow diagram of a process of the prior art showing a two-vessel system with a second vessel in combination with a first hydrochlorination reactor.

As used herein, the term "multihydroxylated-aliphatic hydrocarbon compound" (also abbreviated herein as "MAHC") refers to a compound that contains at least two hydroxyl groups covalently bonded to two separate vicinal carbon atoms and no ether linking groups. MAHC contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3-1,4-, 1,5- and 1,6-diol functional groups as well. Geminal-diols, for example, are precluded from this class of MAHCs.

The MAHCs contain at least 2, preferably at least 3, up to about 60, preferably up to 20, more preferably up to 10, even more preferably up to 4, and yet more preferably up to 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The multihydroxylated aliphatic hydrocarbon, the ester of a multihydroxylated aliphatic hydrocarbon, or the mixture thereof, according to the present invention may be a crude multihydroxylated aliphatic hydrocarbon, the ester of a crude multihydroxylated aliphatic hydrocarbon, or the mixture thereof; and may be obtained from renewable raw materials or biomass.

A "crude" multihydroxylated-aliphatic hydrocarbon product is a multihydroxylated-aliphatic hydrocarbon which has not been submitted to any treatment after its manufacture.

A "purified" multihydroxylated-aliphatic hydrocarbon product is a multihydroxylated-aliphatic hydrocarbon which has been submitted to at least one treatment after its manufacture.

"Renewable raw materials," herein means materials designated as originating from the treatment of renewable natural resources. Among such materials, "natural" ethylene glycol, "natural" propylene glycol, and "natural" glycerol are preferred. Ethylene glycol, propylene glycol and "natural" glycerol are, for example, obtained via the conversion of sugars via known and unknown methods. As described in "Organic Chemistry, 3rd Ed. (Morrison & Boyd, Allyn & Bacon Publishers, 1973, pages 1070-1128)", incorporated herein by reference, these sugars may come from, for example, sucrose sourced from crops such as cane or beets, amylose, glucose or maltose sourced from starch, or cellobiose sourced from cellulose. These sugars can also be obtained from biomass, as described in "Industrial Bioproducts; Today and Tomorrow, Energetics, Incorporated for the U.S. Department of Energy, Office of Energy Efficiency and Renewable Energy, Office of the Biomass Program, July 2003, pages 49, 52 to 56", incorporated herein by reference.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least 2, and preferably at least 3, up to about 60, preferably up to 20, more preferably up to 10, even more preferably up to 4, and yet more preferably up to 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). Dichlorohydrins produced by hydrochlorination of glycerin or glycerin esters include 1,3-dichloro-2-propanol and 2,3-dichloro-1-propanol.

As used herein, the expression "under hydrochlorination conditions" means conditions capable of converting at least 1 wt. %, preferably at least 5 wt. %, more preferably at least 10 wt. % of MAHCs, MCHs, and esters of MAHCs and MCHs present in a mixture and/or feed stream into DCH(s) and/or ester(s) thereof.

As used herein, the term "byproduct(s)" means compound(s) that is/are not chlorohydrin(s) and/or ester(s) thereof and/or chlorinating agent(s) and that do not form chlorohydrin(s) and/or ester(s) thereof under the hydrochlorinating conditions selected according to the present invention.

The expression "heavy byproduct(s)" refer to oligomers of mixture (a) components, such as oligomers of MAHCs and/or esters thereof and oligomers of chlorohydrins and/or esters thereof, and derivatives of such oligomers, such as esters thereof, chlorinated oligomers, and/or chlorinated esters thereof, having a number average molecular weight equal to or greater than the number average molecular weight of the oligomer, such as chlorinated oligomers. The terms chlorohydrin(s), MCH(s) and DCH(s), and ester(s) thereof, are not intended to include heavy byproducts.

The term "epoxide" means a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

As used herein, the expression, "liquid phase" refers to a continuous intermediate phase between gas phase and a solid phase that may optionally comprise a minor amount of gas and/or solid discrete phase(s). The liquid phase may comprise one or more immiscible liquid phases and may contain one or more dissolved solids, such as one or more acids, bases, or salts.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases, two or more liquid discrete phases, and/or two or more solid discrete phases.

As used herein, the expression "plug flow reactor" refers to a reactor or system of reactors, optionally including associated equipment such as, for example, heat exchangers, piping, disengaging vessels, etc., for which the flow pattern through the reactor exhibits a plug flow residence time characteristic.

As used herein, the expression "a plug flow residence time characteristic" refers to residence time distribution of the flow elements such that most of the fluid elements in a vessel or a system of vessels have approximately the same residence time and in the case of a plug flow type of reactor there is also an existence of a composition profile along the flow path such that concentration of the reactants in the fluid decreases from inlet of the system to the outlet of the system and concentration of products increases from inlet of the plug flow system to the outlet of the plug flow system.

A reactor with a plug flow residence time characteristic is a reactor, or system of reactors and/or vessels, for which a step change in a component concentration to the inlet to the reactor or system of reactors and/or vessels is observed at the outlet of the reactor at some multiple of the average residence time of the reactor or system of reactors and/or vessels where 5% of the observed change occurs after at least 0.05 times the average residence time and where at least 87% of the observed change occurs after 2 times the average residence time.

Another embodiment is where 5% of the observed change occurs after at least 0.1 times the average residence time and where at least 90% of the observed change occurs after 2 times the average residence time.

Another embodiment is where 5% of the observed change occurs after at least 0.2 times the average residence time and where at least 95% of the observed change occurs after 2 times the average residence time.

Another embodiment is where 5% of the observed change occurs after at least 0.5 times the average residence time and where at least 90% of the observed change occurs after 1.5 times the average residence time.

Another embodiment is where 5% of the observed change occurs after at least 0.7 times the average residence time and where at least 90% of the observed change occurs after 1.2 times the average residence time.

As the residence time distribution in the vessel is narrowed, efficiency of a plug flow reactor increases and the residence time characteristic approaches the ideal plug flow. The last embodiment stated above has the narrowest residence time distribution of those described. Therefore, a plug flow with the narrowest residence time distribution that can be achieved economically a preferred embodiment of the present invention.

A broad scope of the present invention comprises a process for producing a chlorohydrin by recovering an effluent stream resulting from a hydrochlorination process, and reacting such effluent stream with a multihydroxylated-aliphatic hydrocarbon-containing stream under reaction conditions such that a chlorohydrin is produced.

In order to recover an effluent stream resulting from a hydrochlorination process, a hydrochlorination step must first be carried out. The hydrochlorination reaction step is typically carried out in a hydrochlorination reactor vessel or a series of vessels and the reaction involves converting at least one multihydroxylated-aliphatic hydrocarbon and/or an ester thereof to at least one chlorohydrin and/or an ester thereof, by reacting the multihydroxylated-aliphatic hydrocarbon and/or ester thereof with hydrogen chloride under reaction conditions to produce the chlorohydrin and/or ester thereof. The effluent stream resulting from the hydrochlorination reaction step above is then used in the present invention.

As used herein, the phrase "effluent resulting from the hydrochlorination reaction step" refers to any compound or mixture of compounds coming directly or indirectly from the hydrochlorination reaction step. The effluent may contain for example and non-limitatively at least one compound chosen from chlorohydrin, esters of chlorohydrin, water, catalyst, remaining multihydroxylated-aliphatic hydrocarbon and/or ester thereof, remaining hydrogen chloride, and mixtures thereof. Generally, the effluent coming directly out of the hydrochlorination reactor(s) shall contain a mixture of the abovementioned compounds. This first effluent is subsequently processed through the process of the present invention.

The hydrochlorination reaction effluent stream, contains at least a portion of unreacted chlorinating agent such as an HCl component. The HCl component originates from a chlorinating agent used in the hydrochlorination reaction process.

In one embodiment of the present invention, the effluent stream resulting from a hydrochlorination process is reacted with a multihydroxylated-aliphatic hydrocarbon-containing stream in a reactor vessel; wherein the reactor vessel is a plug flow reactor, under conditions such that at least a portion of any unreacted HCl component present in the effluent stream reacts with a MHAC present in the multihydroxylated-aliphatic hydrocarbon-containing stream to form an amount of a chlorohydrin effluent product stream which exits from the plug flow reactor. Optionally, the product stream may be recovered or passed to a subsequent processing step for example a distillation process.

The effluent stream resulting from a hydrochlorination process may be obtained from any hydrochlorination process well-known in the art. For example, German Patent No. 197308 teaches a process for preparing a chlorohydrin by the catalytic hydrochlorination of glycerin by means of anhydrous hydrogen chloride; WO 2005/021476 describes a continuous process for preparing the dichloropropanols by hydrochlorination of glycerin and/or monochloropropanediols with gaseous hydrogen chloride with catalysis of a carboxylic acid; and WO 2006/020234 A1 describes a superatmospheric pressure process for conversion of a glycerol or an ester or a mixture thereof to a chlorohydrin, comprising the step of contacting a multihydroxylated-aliphatic hydrocarbon, an ester of a multihydroxylated-aliphatic hydrocarbon, or a mixture thereof with a source of a superatmospheric partial pressure of hydrogen chloride to produce a chlorohydrin, an ester of a chlorohydrin, or a mixture thereof in the presence of an organic acid catalyst without substantially removing water; all of the above references are incorporated herein by reference.

The hydrochlorination reaction above may be carried out in a hydrochlorination reactor vessel which may be any well-known reactor vessels such as a single or multiple CSTRs, a single or multiple tubular reactors, or combinations thereof. The hydrochlorination reactor can be, for example, one or more reactors in series or in parallel to each other; a CSTR, a plug flow reactor (PFR), a bubble column reactor; a tubular reactor or a combination thereof.

In an exemplifying hydrochlorination process, a multihydroxylated aliphatic hydrocarbon and a hydrochlorination catalyst are charged to a hydrorchlorination reactor. Then a chlorinating agent such as hydrogen chloride is added to the reactor. The reactor is pressurized at the desired pressure and the reactor contents heated to the desired temperature for the desired length of time. After the hydrochlorination reaction is substantially complete, the reactor contents as a reaction effluent stream is discharged from the reactor and either sent to a separation system, sent to other equipment for further processing, or sent to storage.

In the present invention, at least a portion of the hydrochlorination effluent stream is used as a feed stream to a plug flow reactor along with a multihydroxylated aliphatic hydrocarbon-containing stream to carry out chlorohydrin production in accordance with the present invention as described herein.

Multihydroxylated-aliphatic hydrocarbon compounds useful in the hydrochlorination process of the present invention include for example 1,2-ethanediol; 1,2-propanediol; 1,3-propanediol; 1-chloro-2,3-propanediol, referred to herein as 1-monochlorohydrin; 2-chloro-1,3-propanediol, referred to herein as 2-monochlorohydrin; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the multihydroxylated-aliphatic hydrocarbons used in the present invention include for example 1,2-ethanediol; 1,2-propanediol; 1,3-propanediol; and 1,2,3-propanetriol; with 1,2,3-propanetriol being most preferred.

Examples of esters of multihydroxylated-aliphatic hydrocarbon compounds useful in the hydrochlorination process of the present invention include for example ethylene glycol monoacetate, propanediol monoacetates, glycerin monoacetates, glycerin monostearates, glycerin diacetates, and mixtures thereof. In one embodiment, such esters can be made from mixtures of multihydroxylated-aliphatic hydrocarbons with exhaustively esterified multihydroxylated-aliphatic hydrocarbons, for example mixtures of glycerol triacetate and glycerol.

The "chlorinating agent" as used herein means a hydrogen chloride source for use in the hydrochlorination process of the present invention and which is preferably introduced as a gas, a liquid or in a solution or a mixture, or a mixture thereof, such as for example a mixture of hydrogen chloride and nitrogen gas.

The most preferred hydrogen chloride source is hydrogen chloride gas. Other forms of chloride may be employed in the present invention. Chloride in particular may be introduced with any number of cations including those associated with phase transfer reagents such as quaternary ammonium and phosphonium salts (for example tetra-butylphosphonium chloride). Alternatively, ionic liquids such n-butyl-2-methylimidazolium chloride may be used as a synergist to promote the acid catalyzed displacement of OH from the multihydroxylated-aliphatic hydrocarbon.

Other halide sources may be used which act as co-catalysts for the hydrochlorination of alcohols. In this respect catalytic amounts of iodide or bromide may be used to accelerate these reactions. These reagents may be introduced as gases, liquids or as counterion salts using a phase transfer or ionic liquid format. The reagents may also be introduced as metal salts wherein the alkali or transition metal counterion does not promote oxidation of the multihydroxylated-aliphatic hydrocarbon. Care must be employed in using these co-catalysts in controlled hydrochlorination processes because the potential for RCl (chlorinated organics) formation may increase. Mixtures of different sources of halide may be employed, for example hydrogen chloride gas and an ionic chloride, such as tetraalkylammonium chloride or a metal halide. For example, the metal halide may be sodium chloride, potassium iodide, potassium bromide and the like.

In the hydrochlorination reaction described above, a hydrochlorination catalyst is typically used for carrying out the reaction. The catalyst may be for example a carboxylic acid; an anhydride; an acid chloride; an ester; a lactone; a lactam; an amide; a metal organic compound such as sodium acetate; or a combination thereof. Any compound that is convertable to a carboxylic acid or a functionalized carboxylic acid under the reaction conditions of the hydrochlorination reaction may also be used. Other catalysts useful in the present invention are described in WO 2006/020234 A1, incorporated herein by reference.

The hydrochlorination step of the present invention may include various process schemes, including for example batch, semi-batch, semi-continuous or continuous.

In one embodiment, for example, the present invention includes the hydrochlorination of a multihydroxylated-aliphatic hydrocarbon by reaction with hydrogen chloride in the presence of a hydrochlorination catalyst. The resulting hydrochlorination reaction product is then fed into a plug flow reactor along with a multihydroxylated-aliphatic hydrocarbon-containing stream to further produce a chlorohydrin product stream.

As an illustration, the reaction mixture effluent exiting a dichlorohydrin reactor(s) [for example, a reactor vessel 36 as shown in FIG. 1] described in WO 2006/020234 A1, where primarily dichlorohydrin is formed from the reaction of glycerol and monochlorohydrin with HCl, is a mixture of components containing, for example, dichlorohydrins, monochlorohydrins, glycerol and their esters, catalyst, water and unreacted hydrogen chloride as described above. A significant amount of hydrogen chloride (HCl) remains dissolved and unreacted in the reaction mixture because of phase equilibrium between the liquid and the vapor phases in the hydrochlorination reactor(s). The concentration of HCl present in the liquid phase (reaction mixture) can be, for example, in the range of 5-20% by mass, depending on the exact conditions in the reactor such as temperature, pressure and compositions of liquid and vapor phases in the reactor. The concentration of HCl in the first hydrochlorination reaction effluent can also be in the range of 1-50% by mass. The HCl present in the reaction effluent, if not used efficiently in the process to the maximum possible extent before forwarding the reaction effluent to a distillation column, will exit the distillation system as a light product. This HCl will exit the top of the distillation column either with the dichlorohydrin product or as uncondensed vapors or both. This HCl is a loss for the process if not recovered and recycled to the process. Additionally, this HCl must be neutralized in a downstream process or in suitable equipment if not recovered and recycled, imposing additional expense to the process. If this HCl loss is substantial for the process, then the HCl needs to be recovered and recycled to the process to keep the process economical. Recovering and recycling unreacted HCl from the reaction effluent or the distillation column product is very expensive as HCl is wet and, therefore, very corrosive to the equipment required for recovery. Only equipment made of glass lined, Teflon® lined or other suitable plastic lined materials or of exotic metals and alloys such as tantalum, zirconium and Hastelloy™ can be used in the process for recovering and recycling HCl, imposing a high cost on the process.

Therefore, minimizing HCl in the feed stream to a separation system such as a distillation column without having to recover the HCl is advantageous and overall the least expensive option.

In one embodiment of the process of the present invention, the multihydroxylated-aliphatic hydrocarbon-containing stream may be a glycerol-containing stream [i.e. 1,2,3-propanetriol (glycerol)-containing stream] and the glycerol in the glycerol-containing stream is reacted with any unreacted HCl present in the effluent hydrochlorination stream in a plug flow reactor vessel under the appropriate temperature and pressure. Under the preferred conditions of this embodiment of the present process, the major product is 1-chloro-2,3-propanediol, referred to herein as 1-monochlorohydrin. The minor products of the reaction are 2-chloro-1,3-propanediol, referred to herein as 2-monochlorohydrin, 1,3-dichloro-2-propanol, referred to herein as 1,3-dichlorohydrin and 2,3-dichloro-1-propanol, referred to herein 2,3-dichlorohydrin; Advantageously, the dichlorinated products (1,3-dichloro-2-propanol and 2,3-dichlorol-propanol) are precursors to epichlorohydrin. The dichlorinated products can be readily converted to epichlorohydrin by reaction with a base, as is well-known in the art.

In another embodiment, the glycerol-containing stream may contain monochlorohydrin and/or esters thereof, dichlorohydrin and/or esters thereof, catalyst, ethers, heavies (high molecular weight compounds) and other components.

In still another embodiment, the glycerol-containing stream may be a glycerol-containing stream with a majority (i.e. greater than about 50 wt %) component being glycerol.

The glycerol used in the glycerol-containing stream maybe be crude glycerol, a purified glycerin or a process stream containing glycerin.

The product effluent exiting the plug flow reactor in accordance with the present invention comprises a stream which may contain dichlorohydrins and/or esters thereof, monochlorohydrins and/or esters thereof, unreacted glycerol and/or esters thereof, catalyst, unreacted hydrogen chloride, water, reaction intermediates and optionally ethers and heavies. At least a portion of mainly a dichlorohydrin-containing stream may be recovered from this effluent stream and the remainder of the effluent stream can be recycled to the first hydrochlorination process step which is often a dichlorohydrin-forming reaction; or the remainder can be sent to another processing step or unit. Generally, the effluent exiting the plug flow reactor may be fed into a separation system well known in the art such as a distillation system comprising one or more distillation columns, flash vessels, extraction or absorption columns, or any suitable separation apparatuses known in the art under the conditions to separate the dichlorohydrins product from the other components in the effluent. The dichlorohydrins product separated may include the unreacted chlorinating agent such as hydrogen chloride and water either produced as a byproduct of the hydrochlorination reaction or introduced into the process otherwise.

The dichlorohydrin product of the present invention are useful in the manufacture of epichlorohydrin, giving high yields of high purity epichlorohydrin in short reaction times with low levels of chlorinated by-products that are difficult or expensive to dispose of. The dichlorohydrin product is converted to epichlorohydrin by well known means such as for example by reacting the dichlorohydrin with a base as described in U.S. Pat. No. 4,634,784, incorporated herein by reference.

Then the epichlorohydrin prepared in accordance with the present invention may further converted to an epoxy resin by well know means such as described in Lee and Neville, Handbook of Epoxy Resins, McGraw-Hill Incorporated, 1967, New York, pages 2-2-2-27 incorporated herein by reference.

In one embodiment of the present invention, HCl yield, for example in the glycerol hydrochlorination process, is maximized by reacting the HCl, present in the dichlorohydrin reaction effluent, with glycerol forming monochlorohydrin, the $1^{st}$ reaction step in the hydrochlorination reaction of glycerol to dichlorohydrin. This $1^{st}$ reaction step is carried out in a reactor before feeding the effluent of the dichlorohdrin reactor(s) to the distillation system. These hydrochlorination reactions occur in the liquid phase of the reaction mixture and are dependent on concentration of the reacting species, for example the concentrations of HCl and glycerol in the liquid phase of the reaction mixture.

In accordance with the present invention, the type of vessel that is used for carrying out the present reaction has a large impact on efficiency of the reaction between dissolved HCl contained in the effluent stream from the dichlorohydrin reactor(s) and glycerol in the glycerol-containing stream.

In accordance with the present invention, the overall hydrochlorination process for producing a chlorohydrin is improved by selecting a predetermined type of reactor to be used for reacting HCl with glycerol forming monochlorohydrin, the $1^{st}$ reaction step in the hydrochlorination of glycerol to dichlorohydrin. In accordance with the present invention, using a plug flow type reactor (PFR) for this reaction step provides a huge reduction in the required vessel volume compared to an alternate type of reactor such as a continuous stirred tank reactor (CSTR) for the same reaction efficiency. The reduction in reactor volume can be, for example, five fold depending on specific conditions in the process.

Figure 2:
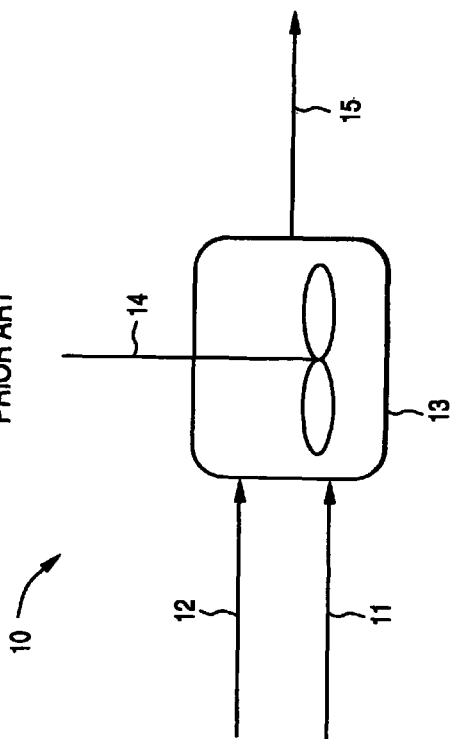
FIG. 2 is a simplified flow diagram of a process showing the use of a continuous stirred tank reactor (CSTR) as an example for reacting dissolved HCl in a reaction effluent with glycerol.

A plug flow type reactor in the present invention is more efficient, much smaller, simpler and cheaper than an alternative such as a CSTR, reducing both capital and operating cost. FIG. 2 shows a CSTR 13 being fed with two reactant streams, a dichlorohydrin (DCH) reactor effluent stream 11 and a glycerol stream 12. The CSTR 13 contains an agitator 14. An effluent product stream 15 exits the CSTR. Another advantage of using a plug flow reactor in the present invention, includes eliminating rotating equipment such as an agitator with a long shaft (agitator 14) that is required in a CSTR. The reliability of the process of the present invention is improved, and the maintenance cost of the present process is reduced. Thus, the prior art hydrochlorination processes may be improved by selecting a specific type of vessel, which comprises a vessel or a system of vessels that exhibit plug flow characteristic, that is most efficient for reacting unreacted dissolved HCl in the dichlorohydrin reactor effluent with glycerol in a glycerol-containing stream.

An ideal plug flow reactor, as described and explained in Chapter 5 of the Chemical Reaction Engineering, $2^{nd}$ edition text book, authored by Octave Levenspiel, refers to a flow pattern in a vessel or a system of vessels such that all elements of a fluid are moving through the vessel or the system of vessels at the same speed such that all fluid elements have the same residence time in the vessel or the system of vessels. A plug flow reactor is also called slug flow, piston flow, ideal tubular and unmixed flow reactor. There may be lateral mixing of fluid in a plug flow vessel but there should be no mixing or diffusion along the flow path. In practice, there is usually some backmixing and diffusion between the flow elements in the direction of the flow resulting in a deviation from an ideal plug flow but it closely approaches an ideal plug flow pattern. This is much different from another type of reactor called a mixed reactor, a back-mixed reactor or a stirred tank reactor, also called continuous stirred tank reactor (CSTR) in which the vessel contents are well stirred and uniform throughout the vessel or the reactor. Thus, the exit stream from this reactor or vessel has the same composition as the fluid within the reactor.

Another characteristic of plug flow reactors or a system of vessels mimicking a plug flow pattern is an existence of a composition profile along the flow path from the inlet of the vessel or a system of vessels to the outlet of the vessel or a system of vessels. Concentration of the reactants decreases from inlet of the vessel or the system of vessels to the outlet of the vessel or the system of vessels along the flow path of the fluid and concentration of the products increases from inlet of the vessel or the system of vessels to the outlet of the vessel or the system of vessels along the flow path of the fluid. In one embodiment of the present invention, for example, the concentration of HCl and glycerol decreases from inlet of a reactor or a system of reactors exhibiting the plug flow characteristic to the outlet of the plug flow reactor or reactor system while the concentration of monochlorohydrin increases from inlet of the plug flow reactor or reactor system to the outlet of the plug flow reactor or reactor system.

The plug flow reactor useful in the present invention may be as simple as a pipe or a tubular reactor or it can be a long and narrow vessel with a sufficient length/diameter ratio to provide a plug flow characteristic; for example, the long and narrow vessel has a length to diameter ratio of at least 4; preferably has a length to diameter ratio of at least 5; more preferably has a length to diameter ratio of at least 7; and even more preferably has a length to diameter ratio of at least 10. The plug flow reactor may contain internals to provide radial mixing, for example, the plug flow reactor may be made with or without packing or baffles in the inside of a cylindrical vessel. A plug flow reactor process can also be simulated by operating several continuous stirred tank reactors in series or a single large vessel having multiple compartments in series and each compartment acting as a CSTR. While the plug flow reactor thus simulated can be used in the present invention, the multiple CSTR arrangement is usually much more expensive than a simpler vessel such as a tubular reactor, a pipe or other simple plug flow reactors. Nevertheless, by "plug flow reactor" as used herein will refer to any of the above types of plug flow reactors or combinations of two or more reactors such as CSTRs, will simulate the performance of a plug flow reactor.

In carrying out the process of the present invention, the two reactant streams can be fed directly to a plug flow reactor. Optionally, the two reactant streams may be mixed together prior to feeding the streams into the plug flow reactor. In one embodiment, the means of mixing the two streams can be provided in the beginning of the plug flow reactor as integral part of the plug flow reactor. Alternatively, an inline static mixer can be used to mix the two streams, the multi-hydroxylated aliphatic hydrocarbon containing stream and the reaction effluent exiting the hydrochlorination reactor(s), before feeding the two streams into a plug flow reactor. An inline static mixer is much simpler and cheaper to operate than a conventional motorized agitator which involves a long shaft as well as a shaft seal and seal flush system. An inline or static mixer may be used to mix two or more streams feeding the plug flow reactor.

In the present process, the plug flow reactor temperature may be controlled as necessary to maximize the reaction efficiency or conversion of the reactants to products. The plug flow reactor can optionally be heated or cooled to control temperature in the reactor, and thereby, control rate of reaction in the reactor. Generally, a temperature of at least about 60° C., preferably a temperature of at least about 80° C., more preferably a temperature of at least about 90° C. and most preferably a temperature of at least about 100° C. is used in the present invention. It is preferable to keep the temperature in the plug flow reactor below about 150° C., preferably below about 140° C. and more preferably less than about 130° C. to minimize formation of undesired byproducts in the process. Operating the plug flow reactor at lower temperatures reduces the risk of a run away reaction in the case of a process upset such as loss of flow or loss of power to the process. Thus, operating the plug flow reactor at lower temperatures improves safety of the process.

Heating or cooling of a plug flow reactor can be achieved by any suitable means known to one skilled in the art such as by providing a jacket on the surface of the plug flow reactor or by providing a pipe or coil inside the reactor wherein the heating or cooling fluid flows through the jacket, pipe or coil. A plug flow reactor can also consist of a shell and tube heat exchanger if there is substantial heat or cooling duty to be provided.

The plug flow reactor may also be operated adiabatically. In this case, the temperature in the plug flow reactor will depend on the temperature of the inlet streams to the plug flow reactor and the extent of conversion in the plug flow reactor. Operating the plug flow reactor adiabatically simplifies design of the plug flow reactor as it eliminates equipment required to control temperature in the plug flow reactor.

In the present process of invention, exact conversion of HCl in the reactor or the reactor system having a plug flow characteristic depends on a number of factors such as residence time, concentration of HCl in the effluent from the first hydrochlorination reactor, temperature, catalyst concentration etc. It is of course desired to have all of the HCl present in the first effluent exiting from a first hydrochlorination reactor converted or depleted by reaction with the multi-hydroxylated aliphatic hydrocarbon present in the multi-hydroxylated aliphatic hydrocarbon-containing stream. However, the HCl depletion may not be complete because of equilibrium limitations in the reactions. Therefore, generally at least about 20% relative conversion of HCl is desired; preferably, at least about 30% relative conversion of HCl is desired; more preferably, at least about 40% relative conversion of HCl is desired; even more preferably, at least about 50% relative conversion of HCl is desired; and most preferably, at least about 80% HCl conversion is desired.

Residence time in the reactor or the reactor system exhibiting a plug flow characteristic is usually less than about 2 hours, often less than about 1 hour, more often less than about 45 minutes, most often less than about 30 minutes, and even more often less than about 20 minutes.

The process of the present invention using a plug flow reactor may be a batch, semi-batch, continuous or semi-continuous process. The process may also include recycle streams in the process.

The equipment and apparatus useful in the process of the present invention may be any well-known equipment in the art and should be capable of handling the reaction mixture at the conditions of the reaction process. Accordingly, in a preferred embodiment of the present invention, the equipment and apparatus of the present invention is at least partially made of or covered with corrosion resistant material and more preferably, the equipment used to perform the process of the present invention is totally made of or covered with corrosion resistant material.

Corrosion resistant materials useful in the present invention may include any material resistant to corrosion known in the art and particularly those materials resistant to corrosion by hydrogen chloride or hydrochloric acid. Non-limiting materials which are resistant to corrosion include those incorporated by reference form Kirk Othmer Encyclopedia of Chemical Technology, in particular those disclosed in Kirk Othmer Encyclopedia of Chemical Technology, $2^{nd}$ Edition, John Wiley and Sons, publishers, 1966 volume 11 and Kirk Othmer Encyclopedia of Chemical Technology, $3^{rd}$ Edition, John Wiley and Sons, publishers, 1980, volume 12.

Suitable corrosion resistant materials include metals such as for example tantalum, zirconium, platinum, titanium, gold, silver, nickel, niobium, molybdenum and mixtures thereof.

Suitable corrosion resistant materials further include alloys containing at least one of the above-mentioned metals. Particularly suitable alloys include alloys containing nickel and molybdenum. Mention can be made particularly of the corrosion resistant metal alloys sold under the names Hastelloy™ or Hastalloy™, which are based on nickel as main ingredient, together with other ingredients, whose nature and percentage depend on the particular alloy, such as for example molybdenum, chromium, cobalt, iron, copper, manganese, titanium, zirconium, aluminum, carbon, tungsten.

Further suitable corrosion resistant materials include ceramics or metallic-ceramics, refractory materials, graphite, glass-lined materials, such as for example enameled steel.

Other suitable corrosion resistant materials include polymers, such as for example polyolefins such as polypropylene and polyethylene, fluorinated polymers such as polytetrafluoroethylene, polyvinylidenefluoride and polyperfluoropropylvinylether, polymers containing sulfur and/or aromatics such as polysulfones or polysulfides, resins such as epoxy resins, phenolic resins, vinyl ester resins, furan resins.

The corrosion resistant materials can be used to make the actual body of the downstream processing equipment devices which need to be protected from corrosion according to the present invention. The corrosion resistant materials can also be used by coating of the surface of such devices.

Mention may be made for example of coatings made from resins. For certain parts such as the heat exchangers, graphite, either impregnated or not, is particularly suited.

Figure 3:
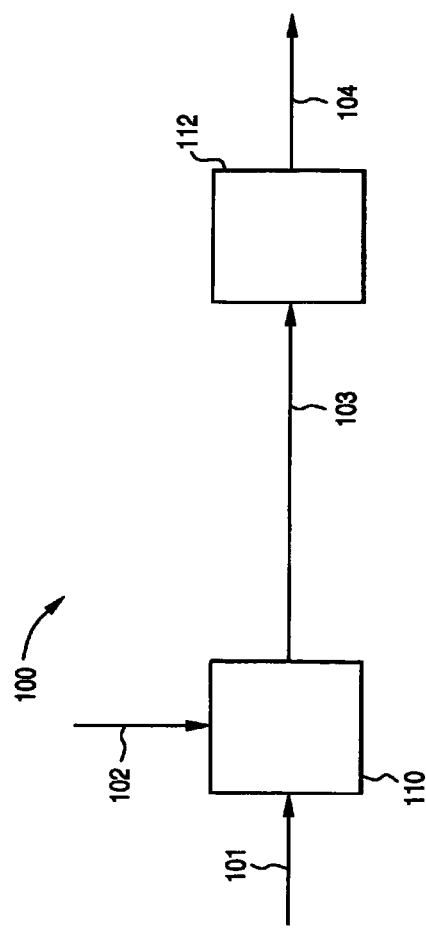
FIG. 3 is a simplified block flow diagram of one embodiment of the process of the present invention showing the use of a plug flow reactor (PFR) for illustration purposes such as for reacting dissolved HCl in a reaction effluent with glycerol.

Referring now to the drawings wherein like numerals indicate like elements, FIG. 3 illustrates a process of the present invention, which is designated generally by the numeral 100. In accordance with one embodiment of the present invention and as shown in FIG. 3, a dichlorohydrin (DCH) reactor effluent stream 101 and a glycerol-containing stream 102 are mixed together in a mixer 110. In this embodiment, a mixer 110 is shown, however, the mixer is an optional piece of equipment and can either be eliminated entirely or made an integral part of the plug flow reactor 112. Other non-limiting pieces of equipment can be added to the present process as will be apparent to those skilled in the art after reading the present invention.

With reference to FIG. 3 again, the mixed stream 103 from the mixer 110 is passed to a plug flow reactor 112 wherein a reaction between the effluent stream 101 and the glycerol-containing stream 102 occurs. The product stream 104 from the plug flow reactor 112 is then passed forward to another unit operation or recovered for further use.

Figure 4:
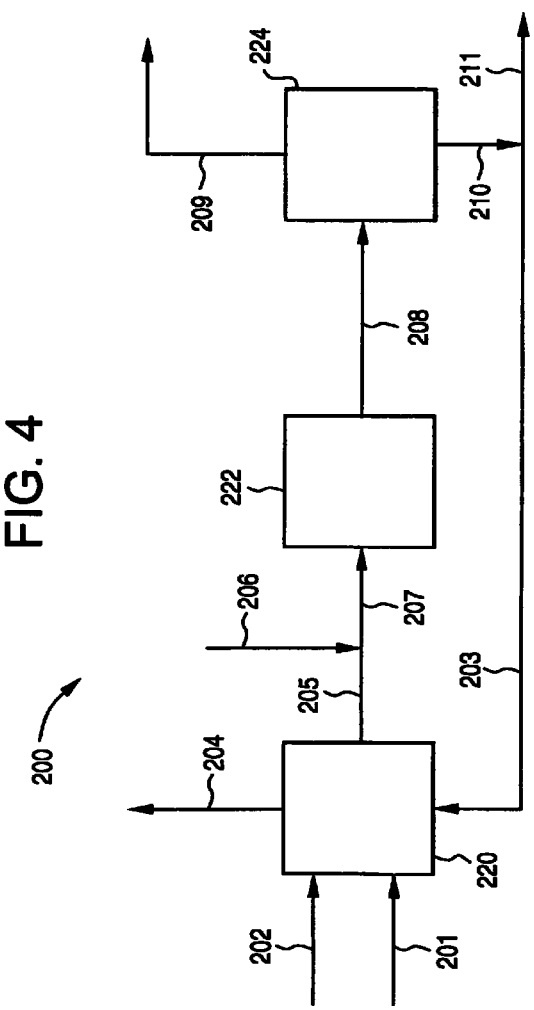
FIG. 4 is a simplified block flow diagram of another embodiment of the process of the present invention showing a process of producing a dichlorohydrin for illustration purposes.

Referring to FIG. 4, there is shown another embodiment of the present invention including for example, a process and apparatus suitable for a continuous and recycle process for preparing a dichlorohydrin (DCH) product that can be further processed to produce an epoxide such as epichlorohydrin. In FIG. 4, the process, generally indicated by numeral 200, includes a catalyst stream 201, an HCl stream 202 and a recycle stream 203 being fed into a DCH reactor 220 with a vent stream 204 coming from the reactor 220. The effluent stream 205 exiting from the reactor 220 is mixed with a glycerol-containing stream 206 and fed as a mixed feed stream 207 into the plug flow reactor 222. The effluent stream 208 from the plug flow reactor 222 is fed into a distillation column 224. A product stream 209 exits the distillation column 224 from the top and a stream 210 exits the column 224 from the bottom. A portion of the bottom stream 210 from the distillation column 224 is recycled as recycle stream 203 to the DCH reactor 220 and a purge stream 211 is fed to a recovery system or passed further to another processing unit. Although not shown in FIG. 4, in another embodiment, optionally, a portion of the glycerin feed may be added to the reactor 220 in combination with any of the incoming streams such as the catalyst in stream 201 or the recycle stream 203 or as a separate glycerine feed stream.

In order to provide a better understanding of the present invention including representative advantages thereof, the following examples are offered. The following examples illustrate the present invention, without limiting the present invention to the examples provided herein.

EXAMPLE 1

In a computer simulated experiment, two separate reactant streams, the first stream being 1.592 kg/hour of an effluent stream (stream 101 in FIG. 3) from a dichlorohydrin producing reactor containing 11.7% by mass HCl and the second stream (stream 102 in FIG. 3) being 0.71 kg/hour of glycerol, were mixed together comprising stream 103 in FIG. 3, containing 8.1% by mass HCl. Composition of the mixed stream 103 is shown in Example 1 in Table 1. The mixed stream 103 was fed into a plug flow reactor (PFR) operating at a temperature of 100° C. and a pressure of 100 psig (791 kPa) and a residence time of 10 minutes. Composition of the effluent stream from the plug flow reactor was estimated by the simulation. Composition of the effluent stream 104 from the plug flow reactor is shown in Example 1 in Table 1. Concentration of HCl in the effluent stream from the plug flow reactor was 3.9% by mass, resulting in HCl conversion of 52%. Concentration of glycerol decreased from 31% by mass to 19% by mass. Concentration of 1-monochlorohydrin increased from 3.2% by mass to 15.6% by mass and the concentration of water increased from 7.9% by mass to 10.1%. Other components in the stream compositions in Table 1 include catalyst, catalyst esters, various ethers and high molecular weight compounds.

COMPARATIVE EXAMPLE A

In another simulated experiment, the same two reactant streams as in Example 1 above, were fed into a continuous stirred tank reactor (CSTR) operating at a temperature of 100° C., a pressure of 100 psig (791 kPa) and a residence time of 10 minutes. Composition of the two streams combined is the same as in the case of PFR and is shown in Comparative Example A in Table 1 for easier comparison with Example 1. Composition of the effluent stream from the CSTR (stream 15 in FIG. 2) was estimated by the simulation and is shown in Comparative Example A in Table 1. Concentration of HCl in the effluent stream from the CSTR was 4.9% by mass which is 1% greater than the HCl concentration in the PFR effluent indicating less conversion of HCl in the CSTR for the same residence time of 10 minutes. Decrease in glycerol content in the CSTR was correspondingly less and increase in monochlorohydrins and water was also less than in the case of PFR in Example 1.

COMPARATIVE EXAMPLE B

In yet another simulated experiment, the same two reactant streams as in Example 1, were fed into a continuous stirred tank reactor (CSTR) operating at a temperature of 100° C., a pressure of 100 psig (791 kPa) and a residence time of 50 minutes. The residence time was thus, five times that in Comparative Example B. Composition of the two streams combined was again the same as in the case of PFR and Comparative Example A and is shown under Comparative Example B in Table 1 for easier comparison with Example 1 and Example A. Composition of the effluent stream from the CSTR (stream 15 in FIG. 2) was estimated by the simulation and is shown in Comparative Example B in Table 1. Concentration of HCl in the effluent stream from the CSTR was 3.9% by mass, the same as in the PFR effluent indicating similar conversion of HCl in the CSTR but at a residence time of 50 minutes.

TABLE I

|  | Example 1 | Comparative Example A | Comparative Example B |
|---|---|---|---|
| Reactor pressure, psig (kPa) | 100 (791) | 100 (791) | 100 (791) |
| Reactor temperature, ° C. | 100 | 100 | 100 |
| Reactor residence time, minutes | 10 | 10 | 50 |
| Total mass flow, kg/hr | 2.302 | 2.302 | 2.302 |

| Stream composition, mass fraction | PFR Inlet stream (103 in FIG. 3) | PFR effluent stream (104 in FIG. 3) | CSTR Inlet streams (11 + 12 in FIG. 1) | CSTR effluent streams (15 in FIG. 1) | CSTR Inlet streams (11 + 12 in FIG. 1) | CSTR effluent streams (15 in FIG. 1) |
|---|---|---|---|---|---|---|
| Glycerol | 0.31 | 0.19 | 0.31 | 0.215 | 0.31 | 0.192 |
| HCl | 0.081 | 0.039 | 0.081 | 0.049 | 0.081 | 0.039 |
| Water | 0.079 | 0.101 | 0.079 | 0.096 | 0.079 | 0.101 |
| 1-monochlorohydrin | 0.032 | 0.156 | 0.032 | 0.126 | 0.032 | 0.142 |
| 2-monochlorohydrin | 0.036 | 0.04 | 0.036 | 0.04 | 0.036 | 0.049 |
| 1,3-dichlorohydrin | 0.406 | 0.413 | 0.406 | 0.413 | 0.406 | 0.416 |
| 2,3-dichlorohydrin | 0.013 | 0.014 | 0.013 | 0.014 | 0.013 | 0.014 |
| Other components | 0.043 | 0.047 | 0.043 | 0.047 | 0.043 | 0.047 |

Comparing the residence time in Example 1 with the residence time in Comparative Example A, shows that a plug flow reactor achieves a much greater conversion of HCl than a CSTR for the same residence time of 10 minutes. Comparative Example B shows that a CSTR requires a residence time of 50 minutes, a five fold increase in residence time, to achieve the same level of conversion as in the plug flow reactor of Example 1. The five fold decrease in the required residence time for the same conversion of HCl by using a plug flow reactor instead of a CSTR, results in a five fold decrease in the reactor volume. The process of the present invention is extremely corrosive and the equipment used in the process requires exotic materials of construction. A five fold decrease in the vessel volume goes a long way in reducing capital cost. Also, a plug flow reactor requires a much simpler construction than a CSTR. A CSTR also requires rotating equipment such as an agitator, further adding to the capital cost and maintenance cost. It is to be understood that the exact decrease in the required reactor volume depends on the specific process parameters such as for example reaction temperature, inlet concentration of HCl, and desired extent of HCl conversion; and the present invention is not to be limited by this example illustrating here the advantage of a PFR.

EXAMPLE 2

In a laboratory experiment, 1.960 kg/hr of a liquid effluent stream from a hydrochlorination reactor (Stream 201) having the composition shown in Table 2 below, was mixed with 0.574 kg/hr of a stream consisting of essentially 100% glycerol (Stream 202), in an inline static mixer. The mixed stream was fed to a plug flow reactor consisting of a 1 inch glass-lined pipe containing mixing elements inside to provide radial mixing. Residence time in the reactor was about 15 minutes. The effluent (Stream 203) from the plug flow reactor contained 3.3% by mass HCl and 8.1% by mass 1-monochlorohydrin (1-MCH). The plug flow reactor was heat traced and temperature of the reactor was controlled at 100° C. Although, not wishing to be bound by this example, % conversion of HCl was 46% in this example. HCl conversion in various cases will depend on several factors such as residence time, concentration of HCl in the effluent from the first hydrochlorination reactor, temperature, catalyst concentration etc.

TABLE II

|  | Stream 201 | Stream 202 | Stream 203 |
| --- | --- | --- | --- |
| Total mass flow, kg/hour | 1.960 | 0.574 | 2.534 |
| Stream composition, mass fraction | | | |
| Glycerol | 0.0 | 1 | 15.6 |
| HCl | 7.9 | | 3.3 |
| Water | 9.4 | | 8.9 |
| 1-monochlorohydrin | 2.3 | | 8.1 |
| 2-monochlorohydrin | 14.2 | | 12.2 |
| 1,3-dichlorohydrin | 41.5 | | 33.1 |
| 2,3-dichlorohydrin | 9 | | 7.1 |
| Other components | 15.5 | | 11.7 |

What is claimed is:

1. A process for producing chlorohydrin comprising;
   (a) reacting (i) a multihydroxylated-aliphatic hydrocarbon-containing stream with (ii) a stream comprising a first effluent exiting from a hydrochlorination reactor; said reaction of step (a) carried out in at least one vessel; wherein the at least one vessel exhibits a plug flow residence time characteristic, and wherein at least a portion of any unreacted hydrochloric acid component present in the first effluent is depleted by a reaction with the multihydroxylated-aliphatic hydrocarbon present in the multihydroxylated-aliphatic hydrocarbon-containing stream to form an amount of monochlorohydrin in a stream comprising a second effluent exiting from the at least one vessel;
   (b) recovering the second effluent from the at least one vessel; and
   (c) optionally passing the second effluent from the at least one vessel to a subsequent processing step; and optionally wherein streams (i) and (ii) are liquid.

2. The process of claim 1, wherein the multihydroxylated-aliphatic hydrocarbon-containing stream and the first effluent stream are mixed together separate from and prior to the streams entering the at least one vessel, and then feeding the mixture of streams into the at least one vessel; or wherein the multihydroxylated-aliphatic hydrocarbon-containing stream and the first effluent stream are mixed together in a mixer wherein the mixer is integral with the at least one vessel.

3. The process of claim 1, wherein the at least one vessel is operated adiabatically or isothermally or with a controlled temperature profile; and wherein the at least one vessel is provided with a means for heating or cooling the contents in the at least one vessel.

4. The process of claim 1, wherein the at least one vessel is two or more vessels in series.

5. The process of claim 1, wherein the multihydroxylated-aliphatic hydrocarbon-containing stream comprises a glycerol-containing stream; or wherein the glycerol-containing stream contains crude glycerol;
   or wherein the glycerol-containing stream is a stream from a renewable resource.

6. The process of claim 1, wherein the first effluent stream exiting from the hydrochlorination reactor contains from 1 wt. % to 50 wt. % hydrochloric acid; and wherein the multihydroxylated-aliphatic hydrocarbon-containing stream contains from 10 wt. % to 100 wt. % of a multihydroxylated-aliphatic hydrocarbon compound.

7. The process of claim 1, wherein the conversion of hydrochloric acid in the at least one vessel is at least 20%.

8. The process of claim 1, (i) wherein the multihydroxylated-aliphatic hydrocarbon-containing stream is maintained at a temperature of from 20° C. to 200° C; and at a pressure of from 0.1 bar (10kPa) to 1000 bar (100MPa); and (ii) wherein the first effluent stream is maintained at a temperature of from 0° C. to 200° C.; and at a pressure of from 0.1 bar (10kPa) to 1000bar (100MPa).

9. The process of claim 1, wherein the total residence time in the at least one vessel is less than 2 hours; and wherein the at least one vessel is operated at a temperature of at least 50° C.

* * * * *